United States Patent [19]

Kraatz et al.

[11] Patent Number: 4,789,746

[45] Date of Patent: Dec. 6, 1988

[54] PROCESS FOR THE PREPARATION OF THE (+)-ANTIPODE OF (E)-1-CYCLOHEXYL-4,4-DIMETHYL-3-HYDROXY-2-(1,2,4-TRIAZOL-1-YL)-PENT-1-ENE

[75] Inventors: Udo Kraatz, Leverkusen; Peter Feyen, Mettmann, both of Fed. Rep. of Germany

[73] Assignee: Bayer Aktiengesellschaft, Leverkusen, Fed. Rep. of Germany

[21] Appl. No.: 835,843

[22] Filed: Mar. 3, 1986

[30] Foreign Application Priority Data

Mar. 19, 1985 [DE] Fed. Rep. of Germany ....... 3509824

[51] Int. Cl.$^4$ ............................................. C07D 24/08
[52] U.S. Cl. .................................................... 548/262
[58] Field of Search ......................................... 548/262

[56] References Cited

U.S. PATENT DOCUMENTS 4,607,108  8/1986  Feyen et al. ........................ 548/262

FOREIGN PATENT DOCUMENTS 0054431  6/1982  European Pat. Off. ............ 548/262
0142566  5/1985  European Pat. Off. .
3302120  7/1984  Fed. Rep. of Germany ...... 548/262

OTHER PUBLICATIONS

Tonno et al., "Asymmetric Reduction of Various, etc." Chem. Pharm. Bull 31 (3) 837 (1983).
Chem. Pharm. Bull., 837 (1983), No. 3, vol. 31, pp. 837–851.

*Primary Examiner*—Glennon H. Hollrah
*Assistant Examiner*—Patricia L. Morris
*Attorney, Agent, or Firm*—Sprung Horn Kramer & Woods

[57] ABSTRACT

A process for the preparation of the (+)-antipode of (E)-1-cyclohexyl-4,4-dimethyl-3-hydroxy-2-(1,2,4-triazol-1-yl)-pent -1-ene of the formula

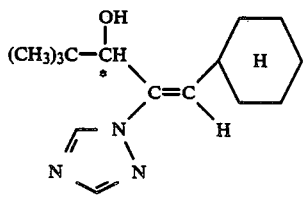

which comprises reacting the (E)-isomer of 1-cyclohexyl-4,4-dimethyl-2-(1,2,4-triazol-1-yl)-pent-1-en-3-one of the formula

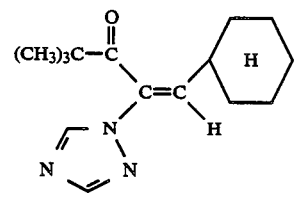

with lithium aluminum hydride in the presence of an inert organic diluent and in the presence of a chiral amino alcohol at a temperature between −80° C. and +50° C. The (+)-antipode is produced in high selectivity, using (+)-N-methyl-ephedrine.

5 Claims, No Drawings

PROCESS FOR THE PREPARATION OF THE (+)-ANTIPODE OF (E)-1-CYCLOHEXYL-4,4-DIMETHYL-3-HYDROXY-2-(1,2,4-TRIAZOL-1-YL)-PENT-1-ENE

The present invention relates to a new process for the preparation of the known (+)-antipode) of (E)-1-cyclohexyl-4,4-dimethyl-3-hydroxy-2-(1,2,4-triazol-1-yl)-pent-1-ene.

As employed herein, the (+)-antipode is that enantiomer which rotates the plane of vibration of linearly polarized light of the sodium D line to the right.

It has already been disclosed that the (+)-antipode of (E)-1-cyclohexyl-4,4-dimethyl-3-hydroxy-2-(1,2,4-triazol-1-yl)-pent-1-ene can be prepared by reacting the corresponding racemic compound with an optically active acid chloride, separating the resulting ester diastereomer mixture by a chromatographic method, and hydrolyzing the ester which contains the (+)-antipode (see U.S. Ser. No. 571,014, filed Jan. 16, 1984, now abandoned.) However, the disadvantage of this process is that it is only suitable for the synthesis of small amounts of the desired antipode.

It has also been disclosed that ketones can be reduced to optically active carbinols with reducing agents in the presence of various chiral auxiliary reagents (see Chem. Parm. Bull. 31, 837 (1983) and EP-OS (European Published Specification) No. 0.054,431). However, the fact that this process is not generally applicable is unsatisfactory. Thus, ketones which do not contain any aromatic groups can only be converted to carbinols with an optical purity insufficient for practical purposes.

It has now been found that the (+)-antipode of (E)-1-cyclohexyl-4,4-dimethyl-3-hydroxy-2-(1,2,4-triazol-1-yl)-pent-1-ene of the formula

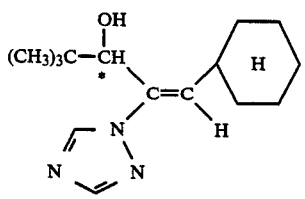

(I)

is obtained by a process in which the (E)-isomer of 1-cyclohexyl-4,4-dimethyl-2-(1,2,4-triazol-1-yl)-pent-1-en-3-one of the formula

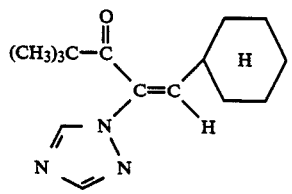

(II)

is reacted with lithium aluminum hydride in the presence of an inert organic diluent and in the presence of a chiral amino alcohol and, if appropriate, in the presence of an amine, at temperatures between −80° C. and +50° C.

It must be regarded as extremely surprising that the (+)-antipode of (E)-1-cyclohexyl-4,4-dimethyl-3-hydroxy-2-(1,2,4-triazol-1-yl)-pent-1-ene of the formula (I) can be prepared by very high yield and excellent purity by the process according to the invention, since, on the basis of the known prior art, it was not to be expected that the reaction would lead selectively to the desired product.

The process according to the invention is distinguished by a number of advantages. Thus, the reactants are obtainable even in relatively large amounts and can also be handled on an industrial scale without problems. Furthermore, the outlay required for carrying out the process in terms of apparatus is small, and working up the reaction mixture obtained when the reaction is complete presents no difficulties. In particular, however, the (+)-antipode of (E)-1-cyclohexyl-4,4-dimethyl-3-hydroxy-2-(1,2,4-triazol-1-yl)-pent-1-ene of the formula (I) can be prepared in higher yield and better optical purity by the process according to the invention than by the method known to date, in which a classical resolution of a racemate is carried out.

Formula (I) gives an unambiguous definition of the (+)-antipode of (E)-1-cyclohexyl-4,4-dimethyl-3-hydroxy-2-(1,2,4-triazol-1-yl)-pent-1-ene which can be prepared by the process according to the invention. In this formula, the asymmetrically substituted carbon atom, which represents the chiral center, is indicated by means of an (*). The letter "E" in front of the systematic name of the compound of the formula (I) indicates that the cyclohexyl radical and the 1,2,4-triazolyl radical are located on *opposite* sides of the double bond.

If lithium aluminum hydride is used as the reducing agent, the (+)-antipode of methylephedrine as the chiral auxiliary reagent, and N-ethylaniline as the additional amine, the course of the process according to the invention can be represented by the following equation:

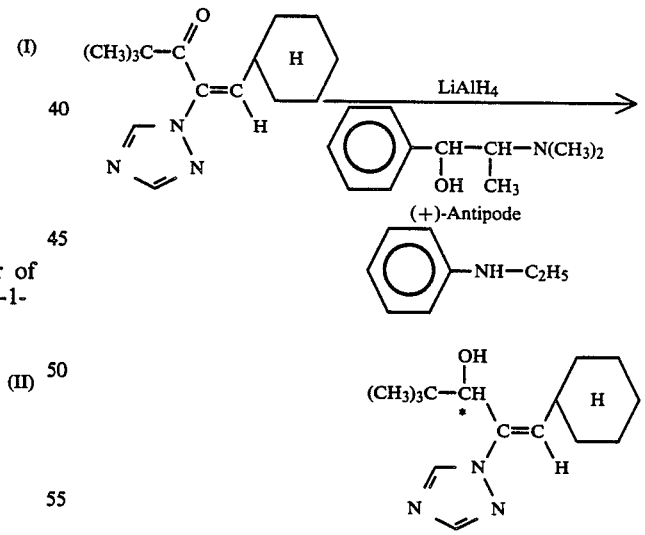

The E-isomer of 1-cyclohexyl-4,4-dimethyl-2-(1,2,4-triazol-1-yl)-pent-1-en-3-one of the formula (II) which is required as the starting material in carrying out the process according to the invention is already known (see DE-OS (German Published Specification) No. 3,322,818).

When the process according to the invention is carried out, lithium aluminum hydride acts as reducing agent.

Diluents which can be employed in the reaction according to the invention are all inert organic solvents customarily used for reactions of this type. Ethers, such as diethyl ether, tetrahydrofuran and tert.-butyl methyl ether, are preferred.

Suitable chiral auxiliary reagents for carrying out the process according to the invention are optically active amino alcohols. The (+)-antipode of N-methyl-ephedrine is particularly preferred.

Amines which, if required, can be employed for carrying out the process according to the invention are preferably secondary amines. N-ethyl-aniline is particularly preferred.

In carrying out the process according to the invention, the reaction temperatures can be varied within a certain range. In general, the reaction is carried out at temperatures between −80° C. and +50° C., preferably between −70° C. and +40° C.

The process according to the invention is generally carried out under atmospheric pressure.

If necessary, a protective gas atmosphere is employed. All customary gases which are inert under the reaction conditions can be employed as protective gases. Nitrogen and argon are preferably used.

In carrying out the process according to the invention, 1 to 5 mols, preferably 2 to 4 mols, of lithium aluminum hydride and 1 to 5 mols, preferably 2 to 4 mols, of a chiral amino alcohol and, if appropriate, 2 to 10 mols, preferably 3 to 8 mols, of an additional amine are generally employed per mol of (E)-isomer of 1-cyclohexyl-4,4-dimethyl-2-(1,2,4-triazol-1-yl)-pent-1-ene-3-one of the formula (II).

In general, the process according to the invention is carried out as follows: the chiral amino alcohol, if appropriate dissolved in an organic diluent, is added dropwise to a suspension of lithium aluminum hydride in an organic diluent at temperatures between 0° C. and 50° C., preferably between 10° C. and 40° C., after which the amine is added if required, and a solution of the (E)-isomer of 1-cyclohexyl-4,4-dimethyl-2-(1,2,4-triazol-1-yl)-pent-1-en-3-one of the formula (II) in an organic diluent is then added dropwise at temperatures between −80° C. and 0° C., preferably between −70° C. and −10° C. Working up is carried out by customary methods. In general, the procedure is as follows: water is added, the reaction mixture is acidified, the organic phase is separated off, the aqueous phase is extracted several times with an organic solvent which is poorly miscible with water, and the combined organic phases are washed and then evaporated down. The residue which remains can be further purified by digestion with suitable organic solvents or by recrystallization.

The (+)-antipode of (E)-1-cyclohexyl-4,4-dimethyl-3-hydroxy-2-(1,2,4-triazol-1-yl)-pent-1-ene of the formula (I) which can be prepared by the process according to the invention, and its use as a fungicide, are known (see DE-OS (German Published Specification) 3,302,120).

The method of carrying out the process according to the invention is illustrated by the example below.

PREPARATION EXAMPLE

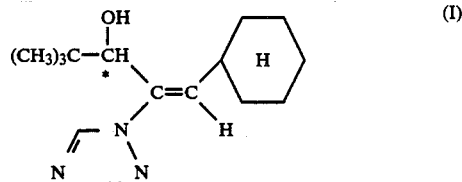

A solution of 12.5 g (70 mmols) of the (+)-antipode of N-methyl-ephedrine in 140 ml of absolute diethyl ether is added dropwise, at 20° C., to a stirred suspension of 2.7 g (70 mmols) of lithium aluminum hydride in 70 ml of diethyl ether. The mixture is heated under reflux for 30 minutes and then cooled to 20° C., 17 g (140 mmols) of N-ethylaniline are added dropwise, and the mixture is allowed to boil under reflux for one hour. Thereafter, the reaction mixture is cooled to −70° C. A solution of 5.2 g (20 mmols) of the (E)-isomer of 1-cyclohexyl-4,4-dimethyl-2-(1,2,4-triazol-1-yl)-pent-1-ene-3-one in 50 ml of absolute diethyl ether is added dropwise at this temperature. Stirring is continued for a further 4 hours at −70° C., and the reaction mixture is then allowed to stand for a further 16 hours at −70° C. Water is then added slowly. The resulting reaction mixture is acidified with 10% strength aqueous hydrochloric acid so that the pH value is about 4. Thereafter, the organic phase is separated off, and the aqueous phase is extracted twice with ethyl acetate. The combined organic phases are washed twice with 5% strength aqueous hydrochloric acid, dried over magnesium sulphate and then evaporated down under reduced pressure. The crystalline residue which remains is stirred with cyclohexane, and the product is filtered off under suction, washed with cyclohexane and dried. 3.2 g (61% of theory) of the (+)-antipode of (E)-1-cyclohexyl-4,4-dimethyl-3-hydroxy-2-(1,2,4-triazol-1-yl)-pent-1-ene are obtained in the form of a crystalline product in this manner.

Melting point: 164.5° C.

$[\alpha]_D^{20} = +81.4°$ (C=0.338 mg/10 ml of CHCl$_3$).

The product has an optical purity of 100%.

It is understood that the specification and examples are illustrative but not limitative of the present invention and that other embodiments within the spirit and scope of the invention will suggest themselves to those skilled in the art.

We claim:

1. A process for the preparation of the (+)-antipode of (E)-1-cyclohexyl-4,4-dimethyl-3-hydroxy-2-(1,2,4-triazol-1-yl)-pent-1-ene of the formula

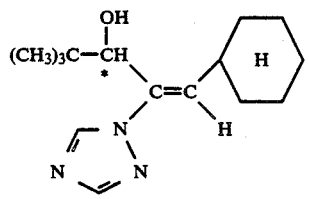

which comprises reacting the (E)-isomer of 1-cyclohexyl-4,4-dimethyl-2-(1,2,4-triazol-1-yl)-pent-1-ene-3-one of the formula

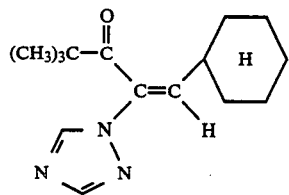

with lithium aluminum hydride in the presence of an inert organic diluent and in the presence of the (+)-antipode of N-methyl-ephedrine and in the presence of N-ethyl-aniline at a temperature between −80° C. and +50° C.

2. A process according to claim 1, wherein the inert organic diluent is diethyl ether, tetrahydrofuran or tert.-butyl methyl ether.

3. A process according to claim 1, wherein the reaction is carried out at a temperature between −70° C. and +40° C.

4. A process according to claim 1, wherein 1 to 5 mols of lithium aluminum hydride and 1 to 5 mols of the N-methyl-ephedrine are employed per mol of the (E)-isomer of 1-cyclo-hexyl-4,4-dimethyl-2-(1,2,4-triazol-1-yl)-pent-1-en-3-one.

5. A process according to claim 4, wherein during the reaction there are also present 2 to 10 mols of the N-ethyl-aniline.

* * * * *